US00PP09078P

United States Patent [19]

Hope

[11] Patent Number: Plant 9,078

[45] Date of Patent: Mar. 14, 1995

[54] ANTHURIUM PLANT NAMED CRYSTAL HOPE

[75] Inventor: Claude Hope, Cartago, Costa Rica

[73] Assignee: Ball Seed Company, Chicago, Ill.

[21] Appl. No.: 181,786

[22] Filed: Jan. 18, 1994

[51] Int. Cl.[6] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

A new and distinct cultivar of *Anthurium crystallinum* plant named Crystal Hope characterized by its outwardly facing leaves which show the full leaf blade, relatively small leaves, iridescent leaf venation which contrasts with dark green leaf blades, leaf petioles, which do not stretch under low light conditions, and by its very infrequent flowering.

1 Drawing Sheet

1

The present invention comprises a new and distinct cultivar of Anthurium, botanically known as *Anthurium crystallinum,* and referred to by the cultivar named Crystal Hope.

The new cultivar was developed by the inventor in Cartago, Costa Rica, through controlled breeding by crossing a selection of *Anthurium crystallinum* identified as LV-36 as the female parent with a selection of *Anthurium crystallinum* identified as LV-40 as the male parent. Both parents were hybrids used only in the breeding program. These parents were noted for their distinctive foliar venation patterns and small leaf size.

The new cultivar was discovered from the progeny of the cross by the inventor in Cartago, Costa Rica, and given the number designation 30-8. Asexual propagation by divisions and micropropagated leaf cuttings first carried out by the inventor in Cartago, Costa Rica, and later carried out in south central Florida and West Chicago, Ill., has demonstrated that the unique features of this new anthurium are stabilized and are reproduced true to type in successive propagations.

The following observations, measurements and values describe plants grown in south central Florida in a polypropylene-covered shade house with day temperatures of 30° to 38° C. and night temperatures of 20° to 30° C. Measurements and values represent averages for six typical plants observed for evaluation purposes.

The following traits have been repeatedly observed to be characteristics which in combination distinguish the new cultivar from other *Anthurium crystallinum* cultivars of the same general type.

1. Relatively small size which is maintained as the plant matures.

2. The leaves face outwardly showing the full leaf blade.

3. The leaf venation is iridescent providing a pleasing contrast with the dark green blade color.

4. Leaf petioles do not stretch under low light interiorscape conditions.

5. More rapid production of finished plants.

6. Very frequent flowering; when flowering does occur, spathes are small and white in color, and the spandix is yellowish white.

All color references are to The Royal Horticultural Society Colour Chart (RHS). Colors will vary somewhat depending on horticultural practices such as light level and fertilization rate, among others, without, however, any variation in genotype.

2

The color photographic drawing comprises a top perspective view showing the inflorescence and foliage of a typical specimen plant of the new cultivar.

The photograph is of a plant of the new cultivar grown in a 25.5 cm pot for one year from a tissue culture plug and grown under appropriate growing conditions. Colors are as accurate as possible with color illustrations of this type.

Origin: Cross between *Anthurium crystallinum selections LV*-36 female parent with LV-40 as male parent.

Classification: *Anthurium crystallinum, cv Crystal Hope*

Propagation: Asexual production either by micropropagation, i.e., tissue culture, or division. Roots are initiated in approximately 20 days at 25° C. The rooting habit is epiphytic, roots emerge from stem, thick velamen.

Plant:

A. *Form.*—Upright

B. *Habit of growth.*—Leaves produced in whorls.

C. *Foliage description.*—Size: 1. Size: a. Length: 20 cm. b. Width: 13.5 cm. 2. Shape:Cordate with two lobes on either side of petiole attachment; apex is acuminate, base is truncate; leaves are oriented outwardly and slightly downwardly. 3. Surface texture: Leaf surfaces are smooth. Veins protrude on top side of leaf; midvein also protrudes on under side but lateral veins are slightly sunken. 4. Margin: Entire. 5. Color: a. Youngest foliage top side; 152A. b. Youngest foliage under side: 199B. c. Expanding foliage top side: 146A. d. Expanding foliage under side: 147C. e. Mature and older foliage top side: Darker and bluer than 147A. f. Mature and older foliage under side: 147B. 6. Petiole.—Length is 20.5 cm, diameter 2 mm; color 7. Venation: Color is generally brilliant crystalline white; for expanding leaves, midveins and main lateral veins are iridescent 192D top side and 147C under side; for mature and older leaves, midveins and lateral veins are iridescent 192D top side and 147B under side; pattern is pinnately reticulate.

Inflorescence:

A. *Flower type and habit.*—Flowers are inconspicuous.

B. *Natural flowering season.*—Year-round in tropical and subtropical areas.

C. *Flowers borne.*—Above foliage, arising from leaf axils.

D. *Peduncle.*—Length is 25.5 cm, diameter 2mm; color 146A.

E. *Quality of flowers.*—Potential of one flower per leaf, although prescence of flowers is infrequent.

F. *Spathe.*—1. Shape: Cordate; apex acuminate, base truncate; spathe is attached from upright to generally perpendicular to peduncle. 2. Size: a. Length: 3.5 cm b. Width: 1.5 cm. 3. Color: White. 4. Surface texture: Top and under surfaces of spathe are smooth.

5. Margin: Entire.

G. *Spadix.*—1. Shape; Cylindrical. 2. Size: a. Length: 2.0 cm. b. Diameter: 2.5 mm. 3. Color: Yellowish white.

Disease resistance:

No fungal, bacterial or viral problems have been observed to date.

It is claimed:

1. A new and distinct cultivar of Anthurium plant named Crystal Hope, as illustrated and described.

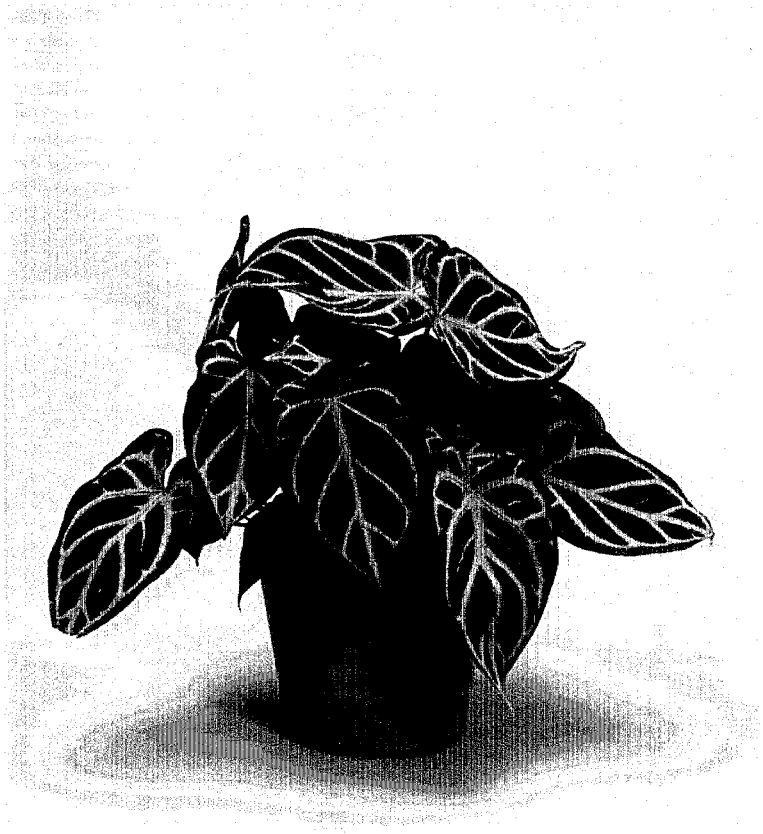

* * * * *